United States Patent [19]

Mitsuhashi et al.

[11] Patent Number: 4,841,779
[45] Date of Patent: Jun. 27, 1989

[54] TENSION TESTER

[75] Inventors: Kenhachi Mitsuhashi; Yoshinobu Ohashi, both of Hiratsuka; Shohei Nakayama, Odawara; Akira Yamada, Tokyo, all of Japan

[73] Assignee: The Yokohama Rubber Co., Ltd., Tokyo, Japan

[21] Appl. No.: 184,631

[22] Filed: Apr. 21, 1988

[30] Foreign Application Priority Data

Apr. 27, 1987 [JP] Japan .................. 62-101845
Jun. 22, 1987 [JP] Japan .................. 62-153480
Mar. 30, 1988 [JP] Japan .................. 63-744489

[51] Int. Cl.⁴ .............................................. G01N 3/08
[52] U.S. Cl. .................................................. 73/826
[58] Field of Search ...................... 73/826, 828, 834

[56] References Cited

U.S. PATENT DOCUMENTS

| | | | |
|---|---|---|---|
| 4,031,746 | 6/1977 | Furuta et al. | 73/834 |
| 4,112,746 | 9/1978 | Itoh et al. | 73/826 |
| 4,572,001 | 2/1986 | Saimoto et al. | 73/826 |

FOREIGN PATENT DOCUMENTS

| | | | |
|---|---|---|---|
| 1084938 | 7/1954 | Fed. Rep. of Germany | 73/826 |
| 56-18086 | 4/1981 | Japan. | |
| 56-19882 | 5/1981 | Japan. | |
| 0184948 | 11/1982 | Japan | 73/826 |
| 0219850 | 9/1986 | Japan | 73/826 |
| 0905707 | 2/1982 | U.S.S.R. | 73/826 |

Primary Examiner—Stewart J. Levy
Assistant Examiner—Michele Simons
Attorney, Agent, or Firm—Armstrong, Nikaido, Marmelstein, Kubovcik & Murray

[57] ABSTRACT

A tension tester in which a specimen marked with at least one measuring marking whose optical characteristic is different from that of the specimen's ground color is held by chucks at the ends and subjected to a tensile load by moving one of the chucks; in which, while the specimen is being stretched, the marking is scanned by a scanner to detect a positional change of the marking in the tensile direction; and in which electric signals which are produced due to the difference in the optical characteristic between the marking and the specimen's ground color are processed to determine the tensile characteristic of the specimen. In this tension tester, the scanner consists of a first scanner with its field of view set to the entire elongation range of the specimen; and at least one second scanner having its field of view set only to a low elongation range of the specimen, the second scanner either having a greater number of elements than the first scanner or being adapted to perform a magnified scanning with greater magnification than that of the first scanner.

18 Claims, 4 Drawing Sheets

TENSION TESTER

BACKGROUND OF THE INVENTION

The present invention relates to a tension tester which measures tensile characteristics of material by using a scanning device such as a television camera, a line sensor camera and a laser scanner camera.

In a tension tester which measures tensile characteristics such as tensile strength, tensile stress and elongation at fracture of materials such as rubber, resin and fiber, a test piece of these materials is held by chucks at the ends and one chuck is pulled to apply a tensile load to the test piece and produce an elongation deformation. With such a tension tester, the process of measuring the tensile stress at, say, 100% elongation requires an inspector to watch the test piece being stretched and determine the point at which the elongation has just reached 100%. This process requires a high level of skill on the part of the inspector, and an unskilled inspector may often produce errors in measurements.

To eliminate the problem of measurement errors which occur depending on the level of skill of the experimenting staff, the inventors of this invention have already proposed tension testers in the Japanese Patent Publications No. 56-19882 and No. 56-18086 in which the test piece is marked with lines which have different optical characteristics from those of the test piece and which are automatically measured by a television camera (hereafter simply referred to as TV camera).

With materials such as rubber which are greatly elongated to 5 to 10 times the original length before being broken, it may sometimes be necessary to investigate the elongation characteristic in a small deformation range as well as in a large deformation range. However, the measurement of tension characteristic during the minute deformation demands higher skills, and the tension tester cited above using a TV camera is appropriate for such measurement. The above-mentioned conventional tension tester using the TV camera, however, has the following disadvantage. That is, when the minute change is measured by putting the camera close to the test piece, the large deformation goes out of sight of the TV camera and cannot be measured. In other words, the conventional testing device cannot take measurement of both minute deformations and large deformations at the same time with a single measurement setting. This lowers the efficiency of experiments. A same as this can also be said of other devices using line sensor camera or laser scanner camera instead of TV camera.

SUMMARY OF THE INVENTION

An object of this invention is to provide a tension tester which can measure minute elongations with high accuracy as well as large elongations.

Another object of the invention is to provide a tension tester which can measure large and small elongations highly accurately at the same time with one measuring operation.

To achieve the above objects, the tension tester of this invention is based on a tension tester in which a specimen marked with at least one measuring marking whose optical characteristic is different from that of the specimen's ground color is held by chucks at the ends and subjected to a tensile load by moving one of the chucks; in which, while the specimen is being stretched, the marking is scanned by a scanner to detect a positional change of the marking in the tensile direction; and in which electric signals which are produced due to difference in optical characteristic between the marking and the specimen's ground color are processed to determine the tensile characteristic of the specimen. In such a tension tester, the scanner consists of at least two scanners, one for covering the entire elongation range of the specimen and at least one for covering only a small elongation range of the specimen, the latter scanner either having a greater number of elements than the former scanner or having a capability of magnified scanning with greater magnification than the former scanner.

The resolution of the scanner which has its field of view set to the small elongation range of the specimen is higher than that of the scanner which covers the entire elongation range. It is thus possible to measure minute elongations of the specimen with a high accuracy by the scanner that covers only the small elongation range. At the same time, large elongations can also be measured highly accurately by the scanner which covers the entire elongation range.

DESCRIPTION OF THE PREFERRED EMBODIMENTS

The scanner employed in this invention generally includes a known TV camera, a line sensor camera (a photoelectric conversion camera using solid state line scanning elements), and a laser scanner camera (a camera consisting of a laser scanner and a light receiver in which the light source side performs scanning). In these scanners, the number of scanning elements in the scanner that has its whole visual field set to the low elongation range is greater than that of a scanner which covers the entire elongation range. For example, in the case of a TV camera, the former scanner has 1024 effective scanning lines, while the latter has only 512 lines. With a line sensor camera, the former has 4096 effective pixels, while the latter has 512 pixels. In the case of a laser scanner camera, the former has a vibration speed of 1/15,000 second per scan, while the latter takes 1/100 second per scan.

The scanner that covers only the low elongation range can be made to perform a magnified scanning by attaching a zoom lens on the camera to obtain a finer measurement than is possible with the scanner that covers the entire elongation range when the two scanners have a same number of elements.

Figure 4A:
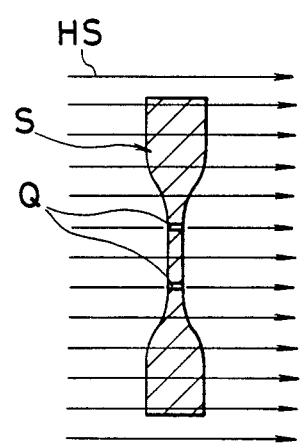
FIGS. 4A and 4B are views, showing the operational principle of the tension tester using a scanner.

The test pieces used in the tension tester are made in compliance with the JIS (Japanese Industrial Standard). One such example is shown in FIG. 4A. On the surface of the test piece or specimen S there are two lines Q, Q spaced longitudinally (in the tensile direction) as markings used for measurement. The color of the marking line Q is different in optical characteristic from the color of the specimen S. It is preferable that the marking line Q be brighter than the specimen's ground color. For example, black or dark color shall be chosen as the ground color of the test piece S, while white or a bright color is used for the marking line Q. The distance or gauge length L between the two lines Q and Q is chosen from among the three values of 20 mm, 25 mm and 40 mm, as defined by JIS.

Figure 5A:
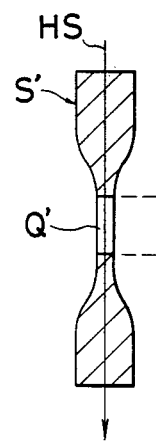
FIGS. 5A, 5B and 5C are views, showing other examples of the operational principle of the tension tester using a scanner.

The marking on the test piece, as shown in FIG. 5A, may be a marking area Q' painted on the test piece S' between the two marking lines Q, Q spaced by the distance L. In this specimen S', the boundary lines at the edges of the marking area Q' correspond to the marking lines Q, Q.

Figure 4B:
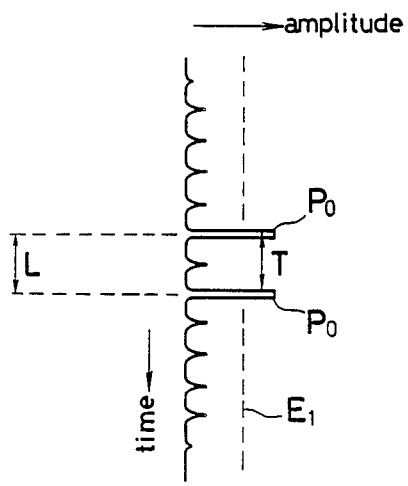

The above-mentioned scanner scans the marking lines Q, Q or marking area Q' on the specimen S or S' subjected to a longitudinal tensile load to measure a change in the distance L between the markings. FIGS. 4A and 4B show the principle of the measuring method, using this scanner.

In FIGS. 4A and 4B, the specimen S under a tensile load is photographed using a TV camera as the scanner and the scanning lines HS of the TV camera are directed perpendicular to the pulling direction of the specimen S. The output signal of the camera will be as shown in FIG. 4B where the level of the signal at points Po, Po that correspond to the marking lines Q, Q is higher than the level at other points. The distance L between the marking lines can be obtained by picking up only the signals that are higher than a certain level E1 by a processing circuit which produces a time signal corresponding to the interval L between the marking lines Q, Q.

Figure 5B:
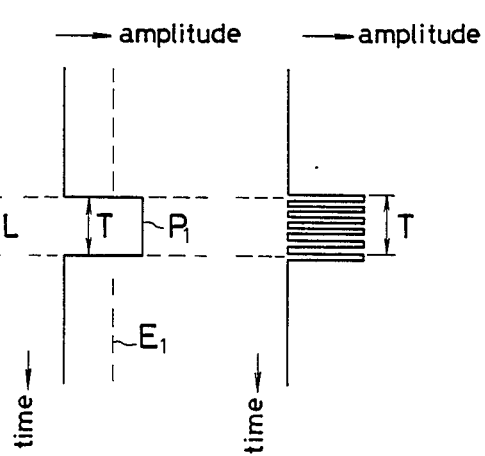
Figure 5C:
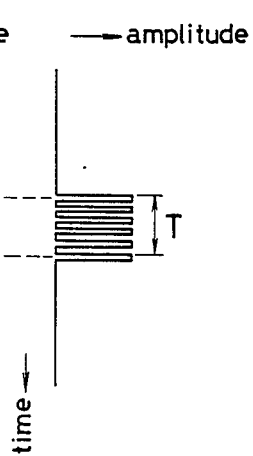

FIGS. 5A, 5B and 5C show the principle on which scanner scans the specimen S', i.e., the scanning lines HS of the scanner are directed in the same direction as the tensile direction of the specimen S'. In this case, the output signal in P1 area corresponding to the marking area Q' is higher in level than those in other areas, as shown in FIG. 5B. As with FIG. 4, it is possible to determine the distance L between the boundaries of the marking area Q' by extracting only those signals from P1 that are higher than a specified level E1 by a processing circuit. The laser scanner camera can also obtain output signals in a similar way.

With the line sensor camera, on the other hand, output signals appear as shown in FIG. 5C, that is, as pulse output signals whose number corresponds to the scan time T over the marked area Q'.

In this tension tester of this invention, the scanner that covers the entire elongation range measures the tensile characteristic of the specimen at a large elongation stage, while the scanner that covers only the minute elongation range measures the tensile characteristic of the specimen at the initial small elongation stage. The resolution l of the scanner is expressed as the ratio of the scanning range H to the number of elements A, i.e., H/A. The scanner for the low elongation range has a narrower scanning range H and a greater number of elements than the scanner for the entire elongation range and thus its resolution is extremely high. With the scanner for magnified scanning, the scan range is narrower than that of the scanner for the entire elongation range, so that it has a similarly high resolution even when they have the same number of elements. Therefore, the scanner for a low elongation range can take highly accurate measurements on the tensile characteristic of the specimen during the initial small elongation stage.

The scanner for the low elongation range views the two marking lines on the specimen at the same time by one camera. As will later be described in connection with a second embodiment of FIG. 2, however, it is also possible to provide two cameras to independently view each of the two marking lines against a reference line marked on separate plates. Checking the marking lines by dedicated cameras independently further increases the accuracy of measurement, as later to be described in greater detail.

In the tension tester of this invention, during the process of pulling the specimen it is desirable to use two different stretching speeds, one at which the specimen is stretched when the scanner for the low elongation range is operating and one at which it is stretched when the scanner for the entire elongation range is operating. That is, when the measurement is taken by the scanner for low elongation range, the specimen is elongated at a low speed and when the specimen has exceeded a prescribed elongation and the scanner for the entire elongation range takes over, the specimen is now elongated at a higher speed.

This switching of stretching speed can further improve the accuracy of measurement. Although the stretching speed varies depending on the kind of specimen, general criteria may be 0.5 to 50 mm/minute for the low elongation range and 50 to 500 mm/minute for the high elongation range which occurs after the low elongation range. The boundary at which the stretching speed is changed is preferably within an elongation range of 1.0 to 50.0%. The stretching speed switching may preferably be accomplished by interlocking two scanners so that one automatically takes over the other.

Now, this invention will be described in connection with the first embodiment shown in FIG. 1.

Figure 1:
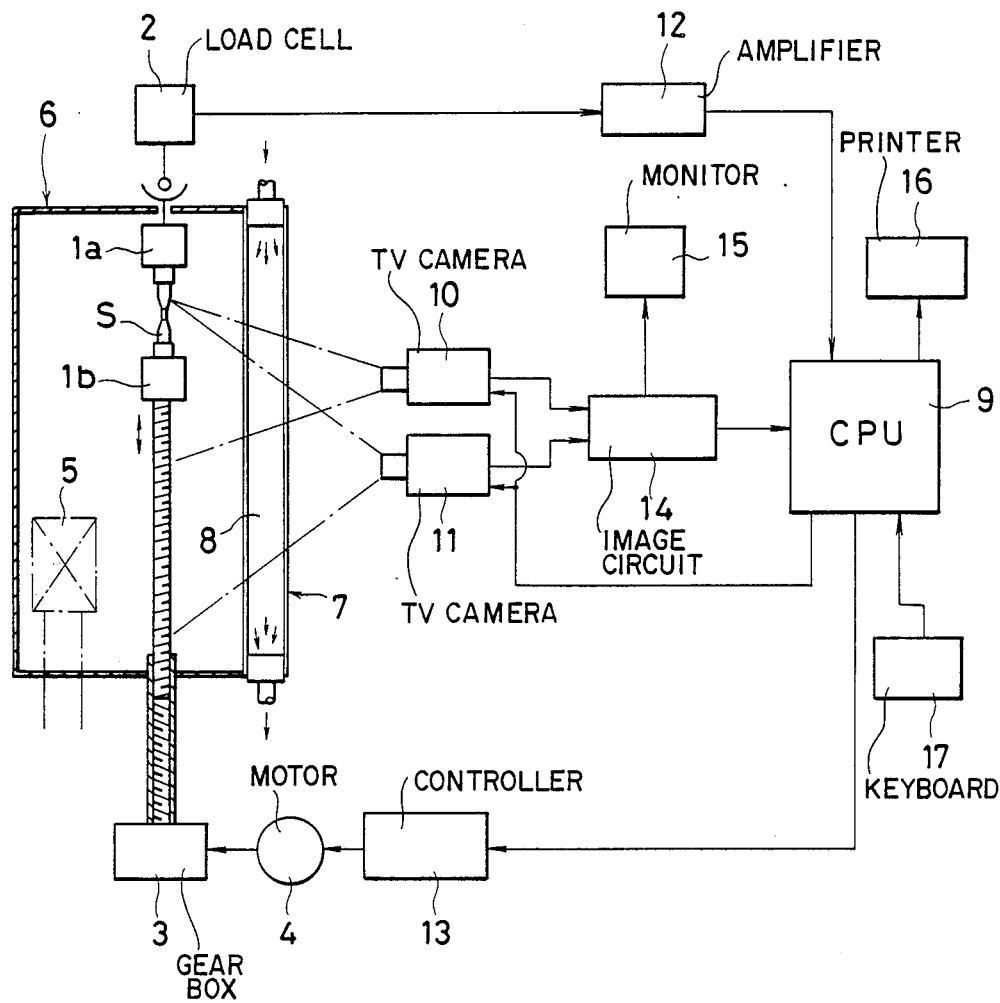
FIG. 1 is a schematic view of a tension tester representing one embodiment of this invention.

In FIG. 1, the reference numeral 1a represents an upper chuck which holds an upper end portion of the specimen S, and 1b designates a lower chuck for holding a lower end portion of the specimen S. The upper chuck 1a is installed stationary at a specified location and has a load cell 2 on its upper side to detect a tensile load. The tensile load detected by the load cell 2 is supplied to the central processing unit 9 through an amplifier 12. The lower chuck 1b is connected to a motor 4 through a gear box 3. The lower chuck 1b is moved up and down by the motor 4 to apply tensile load to the specimen S. The motor 4 is driven by signals from the central processing unit 9 through a motor controller 13.

The upper chuck 1a and the lower chuck 1b form a tension mechanism which is installed in a thermostatic chamber 6 with a built-in cooling coil 5. The thermostatic chamber 6 has on one side thereof a transparent viewing section 7 formed of double glasses through which the interior of the chamber can be seen from the outside. The space 8 between the double glasses of the transparent viewing section 7 is ventilated with hot dry air to prevent dew formation which would cloud the glass surfaces. The thermostatic chamber 6 is used for measuring the material properties at low temperatures or high temperatures and may not necessarily be used for measuring at room temperatures.

On the outside of the transparent viewing section 7, there are two TV cameras 10, 11 as the scanner facing toward the tension mechanism installed inside the chamber. Each of the cameras detects the distance or gauge length L between the marking lines Q, Q on the specimen S in the form of electric signals which are shown for example in FIG. 4B. The detected signals are processed by an image circuit 14 and then fed to the central processing unit 9. Also, the output signal processed by the image circuit 14 can be displayed on a monitor 15. Designated at 16 is a printer which prints out measured values, and 17 is a keyboard to enter data necessary for measurement.

One of the two cameras, 11, is set to cover the entire elongation range of the specimen S to measure changes in the high elongation range of the specimen S. In this embodiment, an ordinary TV camera having 512 effective scan lines is used for the TV camera 11.

On the other hand, the other TV camera 10 is limited to the initial low elongation range to detect changes in the specimen S during the low elongation stage. The TV camera 10 has 1024 effective scan lines, the number being greater than that of the other camera 11. Since it has a larger number of effective scan lines and its visual field is limited to the small elongation range, the TV camera 10 has a significantly higher resolution than the first camera 11, enabling detection of minute changes in the length of the specimen. The TV camera 10 may be attached with a zoom lens as required, which will further increase the accuracy of measurement.

Further, it is possible to use a TV camera 10 which has the same number of effective scan lines as the TV camera 11 and attach a zoom lens to perform magnified scanning.

In this tension tester, the specimen S is arranged so that the distance between marking lines is set to 20 mm according to the prescription under class 3 of JIS and is subjected to a tensile load to elongate by 25% the distance between the marking lines Q, Q from 20 mm to 25 mm. In this low elongation range of 25 mm, the resolution of the TV camera 10 will be 25 mm divided by 1025 lines, i.e., 0.024 mm/line, which is extremely fine.

According to commands from the central processing unit 9, the TV camera 10 is operated in the low elongation range at the initial stage of the tensile test, and as the elongation of the specimen S exceeds a prescribed value, the TV camera 11 takes over to measure the greater elongation. At the same time the camera is switched, the motor controller 13, according to the signal from the central processing unit 9, changes the pulling speed of the lower chuck 1b from the low to the higher normal speed.

Suppose the number of effective scan lines of the TV camera 10 is 400 and that a zoom lens is used to set the entire camera viewing range to 72 mm. Then, the resolution 1 of the TV camera 10 will be 1=H/A=72/400=0.18 mm. Thus, the accuracy of measurement of the TV camera 10 is ±0.9% for the specimen with the gauge length L of 20 mm, ±0.7% for 25 mm, and ±0.45% for 40 mm.

For the TV camera 10 with a zoom lens which has its entire field of view set to 50 mm, the resolution 1 will be 1=H/A=50/400=0.125 mm. Thus, the TV camera 10 has the accuracy of ±0.6% for the specimen with a gauge length L of 20 mm, ±0.5% for 25 mm and ±0.3% for 40 mm. The accuracy is improved over the first TV camera.

As mentioned above, the camera's accuracy can be improved by narrowing the camera's field of view. However, since the gauge length L (distance between the marking lines) as specified by JIS is 20 mm at minimum, further reduction of the view range from the minimum 20 mm is not possible. This means that the upper limit of the accuracy of the scanner of the first embodiment in FIG. 1 is reached at the visual field of 20 mm.

Figure 2:
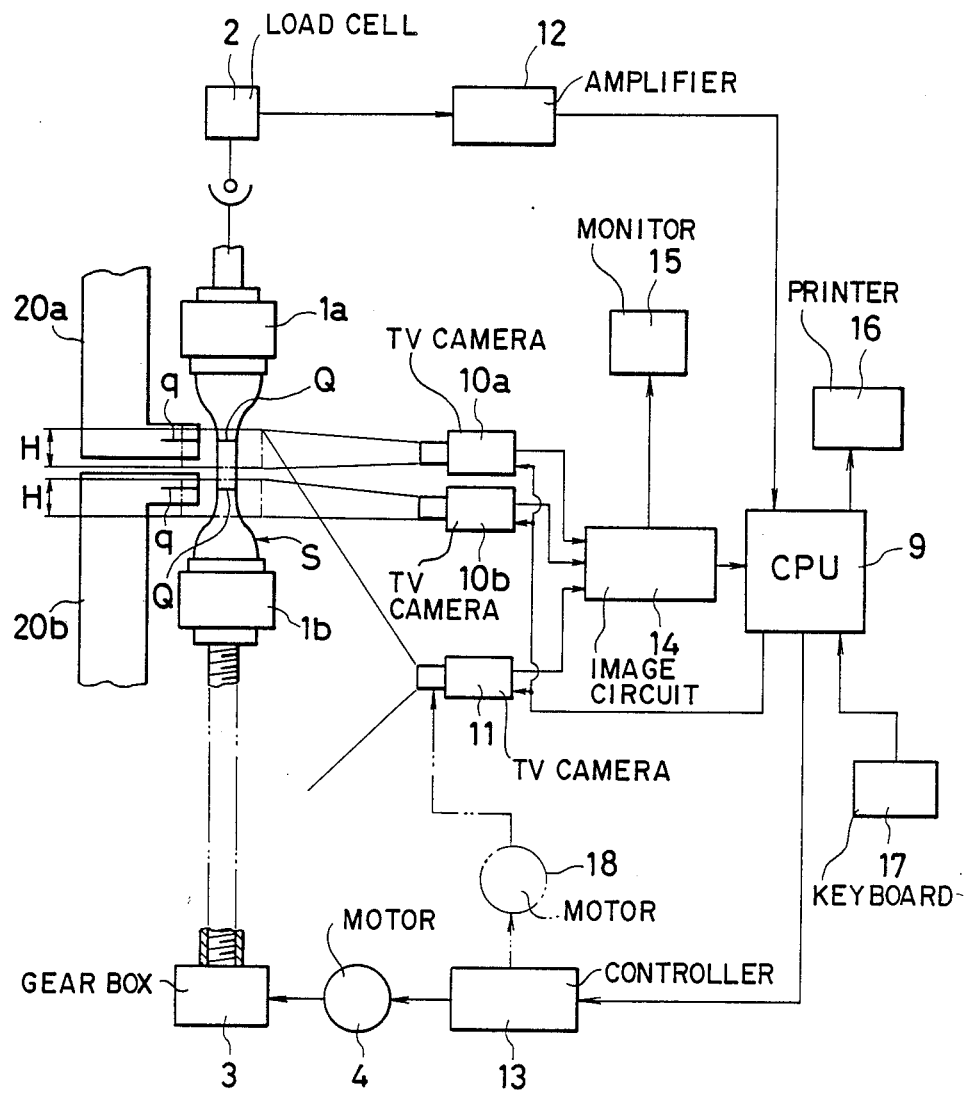
FIG. 2 is a schematic view of a tension tester representing another embodiment of the invention.

FIG. 2 shows a second embodiment which breaks the limit of measurement accuracy inherent in the scanner of FIG. 1 and enables a further improvement of the accuracy.

In the tension tester of FIG. 2, the specimen S held by the upper chuck 1a and the lower chuck 1b is put close to a positional reference plates 20a, 20b which are securely mounted to the equipment frame so that they are stationary. The reference plates 20a, 20b are each marked with a reference line q, which corresponds to each of the two marking lines Q, Q. Although in this embodiment the reference plate is divided into two plates 20a, 20b, it may be formed as a single plate.

With the specimen S arranged as described above, two TV cameras 10a, 10b are installed as scanners which have their entire view fields set to a low elongation range, with the upper and lower TV cameras 10a, 10b, assigned independently to view the upper and lower markings Q, Q on the specimen S respectively.

The entire view fields of the two TV cameras 10a, 10b are each set to a very narrow area H which includes the associated marking line Q. Another TV camera 11 is the same as that of the first embodiment of FIG. 1 and its view field is set to cover the entire elongation range. The TV cameras 10a, 10b, when the number of scan lines is equal to that of the TV camera 11, may be attached with a zoom lens so that it can perform magnified scanning, as with the TV camera 10 in the first embodiment of FIG. 1. These TV cameras 10a, 10b have a larger number of scan lines than the TV camera 11. They may also use a zoom lens to further improve the accuracy.

Figure 3:
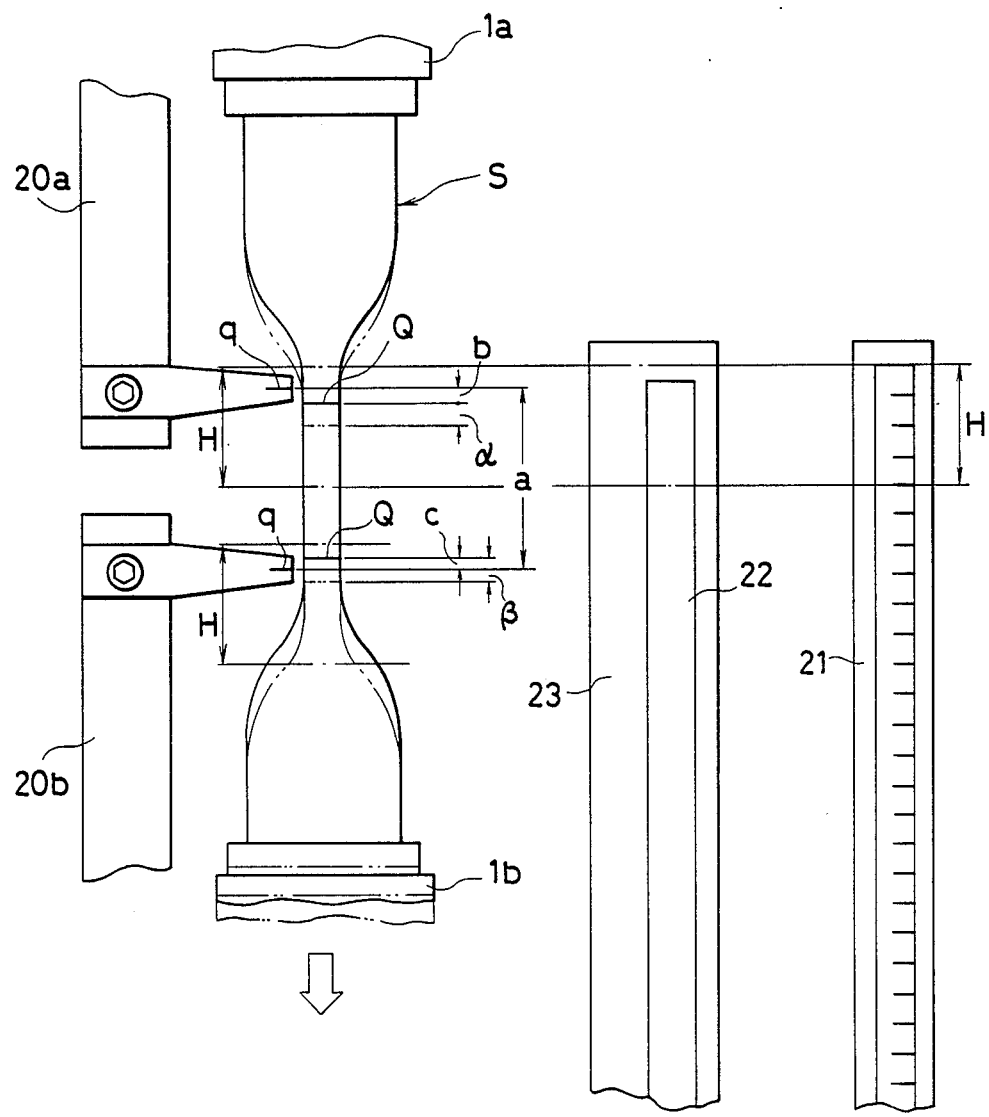
FIG. 3 is an enlarged view of a test piece mounted in the tension tester of FIG. 2.

As shown in FIG. 3, the upper TV camera 10a measures changes in the distance b between the upper marking Q on the specimen S and the reference line q on the positional reference plate 20a; and the lower TV camera 10b measures changes in the distance c between the lower marking Q on the specimen S and the reference line q of the reference plate 20b. From these measurements the elongation of the specimen S can be determined as follows. That is, as the specimen S is slightly elongated, the upper marking Q moves by $\alpha$ and the lower marking by $\beta$. If the distance between the two reference line q, q is a, the gauge length Lo between the initial markings Q, Q is expressed as $$Lo = a - b - c.$$

The length $L_1$ after elongation is given by $$L_1 = a - b - \alpha - c + \beta.$$

Thus, the elongation $\epsilon$ is calculated from $$\epsilon = (L_1 - Lo)/Lo = (\beta - \alpha)/(a - b - c).$$

The distances $\alpha$ and $\beta$ of the upper and lower markings Q, Q from the reference q after the specimen underwent elongation are measured and these measured values are processed by the central processing unit 9 according to the above expression to calculate the elongation $\epsilon$, which is output to the printer 16.

If it is likely that the lightness of the markings Q in contrast to the specimen S is so lowered by disturbance of light from environmental lighting sources or reflected light from the chucks 1a and 1b that the markings Q cannot be precisely detected by the TV cameras 10a and 10b, it may be advantageously devised to avoid such influence of disturbances by making an arrangement as shown in FIG. 3 in which, for example where the specimen S comprises a black rubber and markings Q and Q comprise white markings, there are provided at a side of the specimen S a lightness reference plate 22 having a lightness substantially the same as the lightness of the markings Q and a darkness reference plate 23 having a lightness substantially the same as the lightness of the specimen S. The reference plates 22 and 23 may be arranged only along a low elongation range of the specimen S, but it may more preferably be arranged along a whole elongation range of the specimen. Further, the reference plates 22 and 23 can be advantageously utilized also in connection with the embodiment shown in FIG. 1.

Although in the embodiment shown in FIG. 3 the positional relationship between the reference lines q and markings Q is such that the upper reference q is put higher than the upper marking Q and the lower reference q is put lower than the lower marking Q, the positional relationship is not limited only to this and it may be otherwise.

In the embodiment shown in FIG. 2, the field of view of the TV camera 11 is so fixed as to cover a whole of the elongation range of the specimen S. However, it is feasible not to fix the view field of the TV camera 11 as above but to make it variable by mounting a zoom lens on the camera 11 so that the view field of the TV camera 11 can be expanded in proportion to increasing elongation of the specimen S. As shown by two dot-dash lines in FIG. 2, it is possible to drive the zoom lens by a motor 18 through an automatic control through a motor controller 13 in a manner such that the field changing velocity of the zoom lens is controlled by synchronizing the motor 18 for driving the zoom lens with the motor 4 for driving the chuck 1b. In cases in which the view field of the TV camera 11 is made variable as above, there should necessarily be provided along the entire range of elongation of the specimen a length reference plate such as the one shown at 21 in FIG. 3, and it must be made to visually ascertain the change or elongation of the specimen by incessantly comparing together the degree of elongation and the scale on the length reference plate 21. Further, the reference plate 21 can be advantageously utilized also in cases where the field of view of the TV camera is fixed.

The view field of TV cameras 10a and 10b of the above described tension tester (FIG. 2) can be set free of a restriction of the distance L between the markings Q and Q: In other words, the view field of the cameras can be set to any value shorter than 20 mm, the minimum distance between the markings Q and Q defined according to JIS. Therefore, the view field of the TV cameras 10a and 10b can be set as small as possible, so that the measuring accuracy or precision of the TV cameras can be remarkably enhanced. For example, suppose the TV cameras 10a and 10b each have 400 effective scan lines, are mounted with a zoom lens and have their view field set to 15 mm, which is shorter than the above-mentioned minimum gauge length of 20 mm, then the resolution of the TV cameras 10a and 10b will be $=H/A=15/400=0.0375$ mm. This means that the measuring accuracy will be $\pm 0.18\%$ for the specimen with a gauge length L of 20 mm, $\pm 0.15\%$ for 25 mm and $\pm 0.09\%$ for 40 mm, which shows further improvement over the TV camera of FIG. 1.

As mentioned above, the tension tester of this invention consists of a scanner with its field of view set to the entire elongation range of the specimen and at least one scanner with its view field set to a low elongation range, the latter scanner being provided either with a greater number of elements than the former scanner or with a magnified scanning function. This construction allows a minute elongation in the low elongation range to be measured with a high accuracy by the latter scanner and at the same time permits the normal large elongation to be detected by the former scanner without any problem. To state more concretely, it is possible to read minute elongation (0.2 to 20%) in the low elongation range with a high accuracy within $\pm 0.2\%$ and large elongation (20 to 600%) in the normal elongation range with an accuracy within $\pm 1\%$. In addition, these measurements in two different elongation ranges can be done simultaneously with a single measuring operation.

We claim:

1. In a tension tester in which a specimen marked with at least one measuring marking whose optical characteristic is different from that of the specimen's ground color is held by chucks at the ends and subjected to a tensile load by moving one of the chucks; in which, while the specimen is being stretched, the marking is scanned by a scanner to detect a positional change of the marking in the tensile direction; and in which electric signals which are produced due to difference, in optical characteristic between the marking and the specimen's ground color are processed to determine the tensile characteristic of the specimen; said tension tester comprising:
   a first optical scanner with its viewing field set to include an entire elongation range of the specimen; and
   at least one second optical scanner with its viewing field set to include only a low elongation range of the specimen, the second scanner having a greater number of scanning lines than that of the first scanner.

2. A tension tester as set forth in claim 1, wherein said at least one second optical scanner that covers only the low elongation range measures a distance defined by said at least one measuring marking on the specimen.

3. A tension tester as set forth in claim 1, wherein said at least one measuring marking includes an upper marking and a lower marking, the second optical scanner covering only the low elongation range consists of at least two optical scanners, one optical scanner being fixed in position for scanning the upper marking on the specimen with respect to the tensile direction and the other optical scanner being fixed in position for scanning the lower marking with respect to the tensile direction, and reference plates having reference lines marked thereon which are to be compared with the upper and lower markings are put close to the specimen.

4. A tension tester as set forth in claim 1, wherein the rate at which the specimen is pulled is changed in such a way that the pulling speed is low when the specimen is scanned by the optical scanner that covers only the small elongation range and it is increased when the specimen is scanned by the optical scanner that covers the entire elongation range of the specimen.

5. A tension tester as set forth in claim 4, wherein the pulling speed is 0.5 to 50 mm/minute in the low elongation range and 50 to 500 mm/minute in the higher elongation range that occurs after the low elongation range.

6. A tension tester as set forth in claim 1, wherein the optical scanners are either television cameras, line sensor cameras or laser scanner cameras.

7. A tension tester as set forth in claim 3, wherein the view field of the first optical scanner is variable according to a change of elongation of the specimen.

8. A tension tester as set forth in claim 7, wherein a length reference plate is provided along the entire elongation range of the specimen.

9. A tension tester as set forth in claim 3, wherein a lightness reference plate and a darkness reference plate are provided along at least a low elongation range of the specimen.

10. In a tension tester in which a specimen marked with at least one measuring marking whose optical characteristic is different from that of the specimen's ground color is held by chucks at the ends and subjected to a tensile load by moving one of the chucks; in which, while the specimen is being stretched, the marking is scanned by a scanner to detect a positional change of the marking in the tensile direction; and in which electric signals which are produced due to the difference in the optical characteristic between the marking and the specimen's ground color are processed to determine the tensile characteristic of the specimen; said tension tester comprising:

a first optical scanner with its viewing field set to an entire elongation range of the specimen; and at least one second optical scanner with its viewing field set to include only a low elongation range of the specimen, the second scanner being adapted to perform a magnified scanning with greater magnification than that of the first optical scanner.

11. A tension tester as set forth in claim 10, wherein said at least one second optical scanner which covers only the low elonation range measures a distance defined by said at least one measuring marking on the specimen.

12. A tension tester as set forth in claim 10, wherein said at least one measuring marking includes an upper marking and a lower marking, the second optical scanner covering only the low elongation range consists of at least two optical scanners, one optical scanner being fixed in position for scanning the upper marking on the specimen with respect to the tensile direction and the other optical scanner being fixed in position for scanning the lower marking with respect to the tensile direction, and reference plates having reference lines marked thereon that are to be compared with the upper and lower markings are put close to the specimen.

13. A tension tester as set forth in claim 10, wherein the rate at which the specimen is pulled is changed in such a way that the pulling speed is low when the specimen is scanned by the scanner that covers only the small elongation range and it is increased when the specimen is scanned by the scanner that covers the entire elongation range of the specimen.

14. A tension tester as set forth in claim 13, wherein the pulling speed is 0.5 to 50 mm/minute in the low elongation range and 50 to 500 mm/minute in the higher elongation range that occurs after the low elongation range.

15. A tension tester as set forth in claim 10, wherein the optical scanners are either television cameras, line sensor cameras or laser scanner cameras.

16. A tension tester as set forth in claim 12, wherein the view field of the first optical scanner is variable according to a change of elongation of the specimen.

17. A tension tester as set forth in claim 16, wherein a length reference plate is provided along the entire elongation range of the specimen.

18. A tension tester as set forth in claim 12, wherein a lightness reference plate and a darkness reference plate are provided along at least a low elongation range of the specimen.

* * * * *